United States Patent [19]

Palmaer

[11] 4,186,447
[45] Feb. 5, 1980

[54] EAR PROTECTOR ATTACHMENT FOR A HELMET

[76] Inventor: Tore G. Palmaer, S-330 30 Gnosjö, Sweden

[21] Appl. No.: 916,547

[22] Filed: Jun. 19, 1978

[30] Foreign Application Priority Data

Jul. 1, 1977 [SE] Sweden .............................. 7707662

[51] Int. Cl.$^2$ ................................................ A42B 3/00
[52] U.S. Cl. ........................................ 2/423; 2/209; 179/156 R
[58] Field of Search .................... 179/156 A, 156 R; 2/209, 174, 6, 422, 423, 424

[56] References Cited

U.S. PATENT DOCUMENTS

| | | | |
|---|---|---|---|
| 3,721,993 | 3/1973 | Lonnstedt | 2/423 |
| 4,027,341 | 6/1977 | Patteri | 2/209 X |
| 4,069,512 | 1/1978 | Palmaer | 2/423 X |

*Primary Examiner*—Werner H. Schroeder
*Assistant Examiner*—Andrew M. Falik

[57] ABSTRACT

A device for holding an ear defender includes a housing with a space therein to accommodate a loop which forms part of a supporting member for an ear defender. The space is defined by a bottom wall, a rear wall, and a front wall, the front wall having notches to receive part of the supporting member connected to the loop. The loop is provided with two journalling parts which are arranged in line with each other and which are arranged in a groove on the inside of the front wall to thereby provide a journalling axis for the supporting member. An aperture is formed in the housing to extend through the bottom wall, and a central pin is positionable in the aperture for the purpose of affixing the device to a helmet. A lever is pivotably journalled with one end in the space for housing near the inside of the rear wall and the other end arranged to receive a transverse spring section of the loop. The spring section is arranged to press against the lever which is adapted to be moved through a dead center condition between two positions, the supporting member being thus pivotable about its journalling axis between two distinct positions.

4 Claims, 3 Drawing Figures

EAR PROTECTOR ATTACHMENT FOR A HELMET

BACKGROUND OF THE INVENTION

This invention relates to ear defenders, and more particularly to means for holding an ear defender, said holder being secured to a helmet by means of a central pin.

OBJECT OF THE INVENTION

It is one object of this invention to provide an improved ear defender.

SUMMARY OF THE INVENTION

According to this invention, there is provide a device for holding an ear defender, said device comprising a housing with a space therein to accommodate a loop forming part of a supporting member for an ear defender. The space is defined by a bottom wall, a rear wall and a front wall having notches to receive parts of the supporting member connected to the loop; the loop having two journalling parts arranged in line with each other which are arranged in a groove on the inside of the front wall to provide a journalling axis for the supporting member. An aperture is formed in the housing to extend through the bottom wall and a central pin is positionable in the aperture for the purpose of affixing the device to a helmet. A lever is pivotably journalled with one end in the space of the housing near the inside of the rear wall, the other end being arranged to receive a transverse spring section of the loop. Said spring section is arranged to press against the lever which is adapted to be moved through a dead center condition between two positions; the supporting member being thus pivotable about its journalling axis between two distinct positions.

A preferred embodiment of this invention comprises an improved holder for protective ear defenders enabling the ear defender to press sufficiently hard for all normal face widths, enabling the helmet to be raised or lowered on the wearer's brow without the ear defenders altering position, enabling the ear defenders to be swung out away from the ears to a specific position when desired, enabling the ear defenders to be folded back to a rest position on the helmet without noticeably obstructing the rim of the helmet, and enabling the ear defenders to be snapped in against the helmet in this rest position to protect them from rain.

BRIEF DESCRIPTION OF THE DRAWINGS

In order that the invention may be more readily understood, and so that further features thereof may be appreciated, the invention will be further described by way of example with reference to one embodiment of a means according to the invention shown in the drawings, in which.

DESCRIPTION OF PREFERRED EMBODIMENT

Figure 1:
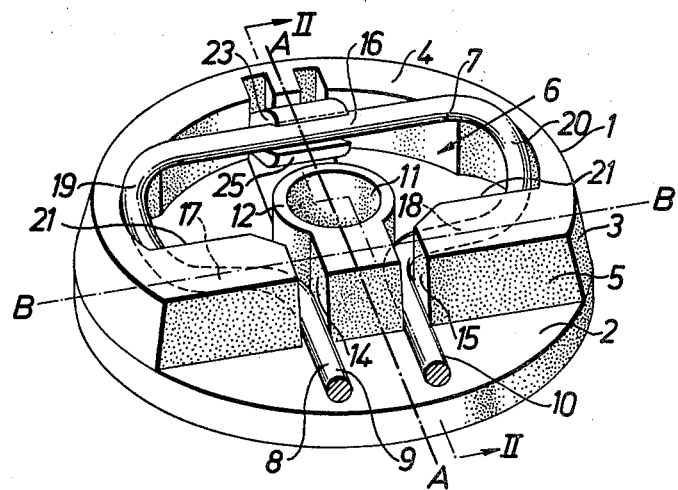
FIG. 1 shows in perspective the journalling housing with a part of the yoke of the ear defender.

Referring to the drawings journalling housing for a protective ear defender holder is designated 1, the holder being attached to a helmet in suitable manner. The housing has a circular bottom plate 2 and a section 3 protruding from this section 3 and comprising a rear wall 4, bent or curved, with somewhat more than semi-circular extent, and a front, straight wall 5, extending between and joining the ends of the curved wall 4. The curved wall 4 and the transverse wall 5 thus surround a space 6 to receive a loop 7, which is a part of a wire yoke 8 carrying the ear defenders of the hearing protection means. Two legs 9, 10 of the wire yoke extend into said loop 7. The journalling housing 1 is also provided with a central aperture 11 surrounded by a cylindrical part 12 connected with the transverse wall 5, the aperture 11 being arranged to receive a central pin 13 by means of which the journalling housing 1 is pivotably journalled to a holder which in turn is secured to the helmet, possible via a separate attachment plate arranged on the helmet without any holes being made therein.

The two legs 9, 10 of the wire yoke are received in notches 14, 15 in the transverse wall 5, these notches being open at the top and located one on each side of a center line A—A running through the center of the journalling housing and through the mid-point of the transverse wall 5. The loop of the wire yoke comprises a spring section 16 running transverse to the symmetrical dividing line of the yoke and journalling parts 17, 18 arranged in line with each other and joining the loop 7 to the legs and arranged perpendicular to the center line A—A (or the symmetrical dividing line of the wire yoke), and two opposed arc sections 19, 20 joining the transverse spring part 16 to the two journalling parts 17 and 18, respectively.

Close to the bottom plate 2 on the inside 21 facing the space 6, the transverse wall 5 is provided with two grooves 22 aligned with each other, forming the seat and journalling center for the two journalling parts 17, 18 of the loop. The yoke is thus pivotable about an axis coinciding with the common center line B—B of the journalling parts, said journalling axis B—B thus intersecting at right angles said center line A—A of the journalling housing. It will be understood that the loop and the legs 9, 10 of the yoke are in different planes which form an obtuse angle with each other (150°–170°, for instance), depending on the swing desired or required for the ear defenders.

Figure 2:
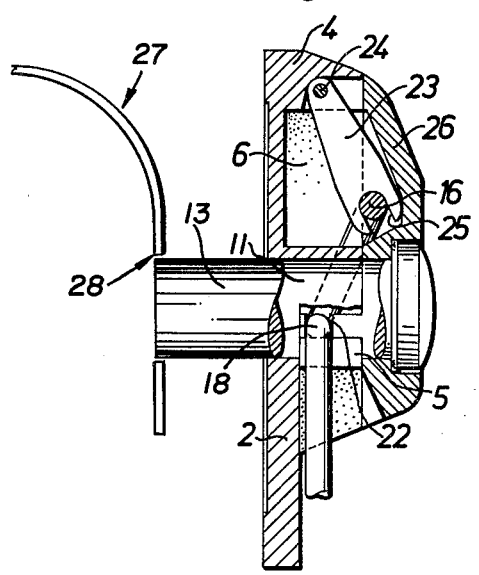
FIG. 2 shows the bearing housing in section along the line II—II in FIG. 1, but closed by a lid so that the yoke assumes one of its distinct positions; and with the central pin positioned within the opening of a helmet to affix the housing releasably thereto.
Figure 3:
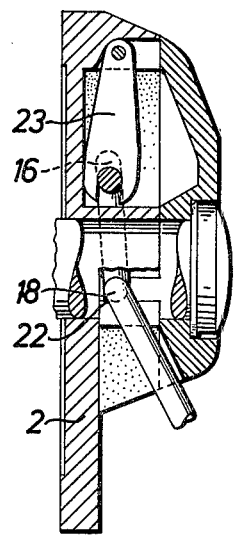
FIG. 3 shows a section through journalling housing as in FIG. 2 but with the yoke in its second distinct position.

A rigid lever 23 is arranged opposite the transverse wall 5 in the space 6 in line with said center line A—A, one end of said lever being pivotably journalled in the curved wall 4 by means of a pin 24 extending substantially parallel to the journalling axis formed by the two journalling parts of the loop. The other end of the lever 23 is provided with a recess 25 open at the front, to receive the transverse spring part 16 in free engagement. The space 6 is sufficiently deep to allow the engagement end of the lever 23 and the spring part 16 received thereby to pass a connecting line extending between the pin 16 of the lever and the journalling axis determined by the journalling parts of the loop 7 so that these journalling parts, and thus the loop, can assume two distinct poisitions on either side of this connecting line due to the increasing spring force applied on the lever 23 by the spring part 16 of the loop, during its passage of said connecting line. A certain spring force also exists when the parts assume their distinct outer positions, particularly the position shown in FIG. 3. Thus the arrangement possesses a dead center condition when being moved from the initial position to the final position. The legs 9, 10 of the yoke and the ear defenders carried thereby will thus also assume two distinct positions, i.e. a folded down position as shown in FIG. 2 and folded out position as shown in FIG. 3.

The journalling housing is covered by a lid 26, the journalling housing and lid being pivotably journalled on a helmet 27 having an opening 28 in the sidewalls thereof dimensioned to releasably receive central pin 13 or a special attachment piece by means of the central pin 13 so that the ear defender can also be turned (friction connection) between a rear position of rest on the helmet and a front position covering and protecting the ear. This movement is considerably facilitated since the ear defender can assume an outer, out-swing position as shown in FIG. 3 in which the defender can pass the rim of the helmet and there is no risk of damage or unnecessary wear on the journalling housing or yoke since hardly any force need be applied for movement between the positions, as was necessary with previously known holders.

The bearing housing and yoke are in practice constructed so that when pressed or snapped into position (FIG. 2) the ear defender abuts the head for all normal face widths with a pressure of around 1 kgf. The journalling housing is pivotable about its center (determined by the central pin 13) in relation to the helmet so that the helmet can be raised or lowered on the brow without the position of the ear defenders being disturbed. As each ear defender is pulled away from the ear with a force of about 1.5 kgf, it snaps out to the outer position permitting ventilation of the ear, and can then be snapped back again to its protective position over the ear by pressing in the ear defender with a force of around 0.5 kgf. When the ear defender has been folded back to the rear position, it should preferably be snapped in against the helmet to provide efficient sealing against water, protecting the inside of the ear defender.

I claim:

1. A device for holding an ear defender, said device comprising a housing having a space therein to accommodate a loop forming part of a supporting member for an ear defender, said space being defined by a bottom wall, a rear wall and a front wall of said housing, said front wall having notches, formed therein to receive parts of the supporting member connected to the loop, the loop having two journalling parts arranged in line with each other which are arranged in a groove on the inside of the front wall to provide journalling axis for the supporting member, a lever pivotably journalled with one end being arranged to receive a transverse spring section of the loop, said spring section being arranged to press against the lever which is adapted to be moved through a dead center condition between two positions, the supporting member being pivotable about its journalling axis between the distinct positions.

2. A device according to claim 1 when mounted on a helmet.

3. A device according to claim 1 wherein said housing is provided with an aperture extending through said bottom wall between said front and rear walls, and a central pin positionable in said aperture for attaching the device to a helmet.

4. A device according to claim 2, wherein both the supporting member and the journalling housing are pivotably arranged together about the central pin.

* * * * *